(12) United States Patent
Amamiya et al.

(10) Patent No.: US 9,709,489 B2
(45) Date of Patent: Jul. 18, 2017

(54) DEVICE FOR MEASURING POLARIZATION DEGREE AND REFRACTIVE INDEX

(71) Applicant: ATAGO CO., LTD., Tokyo (JP)

(72) Inventors: Hideyuki Amamiya, Tokyo (JP); Masanosuke Tanaka, Tokyo (JP)

(73) Assignee: ATAGO CO., LTD. (JP)

( * ) Notice: Subject to any disclaimer, the term of this patent is extended or adjusted under 35 U.S.C. 154(b) by 0 days.

(21) Appl. No.: 14/895,305

(22) PCT Filed: Jun. 1, 2015

(86) PCT No.: PCT/JP2015/065755
§ 371 (c)(1),
(2) Date: Dec. 2, 2015

(87) PCT Pub. No.: WO2015/186655
PCT Pub. Date: Dec. 10, 2015

(65) Prior Publication Data
US 2017/0074791 A1    Mar. 16, 2017

(30) Foreign Application Priority Data

Jun. 2, 2014  (JP) .................................. 2014-114113

(51) Int. Cl.
*G01N 21/00*    (2006.01)
*G01N 21/41*    (2006.01)
(Continued)

(52) U.S. Cl.
CPC ............ *G01N 21/4133* (2013.01); *G01J 4/04* (2013.01); *G01N 21/21* (2013.01); *G01N 33/02* (2013.01);
(Continued)

(58) Field of Classification Search
CPC ........ G01N 21/42; G01N 21/21; G01N 21/65; G01N 3/02; G01J 4/04; G01J 3/02; G01J 3/51
See application file for complete search history.

(56) References Cited

U.S. PATENT DOCUMENTS

2009/0323071 A1\* 12/2009 Kuwahara .......... G01N 21/0332
356/445
2011/0246091 A1   10/2011 Fedele

FOREIGN PATENT DOCUMENTS

JP    S56117151 A    9/1981
JP    S5817342 A    2/1983
(Continued)

OTHER PUBLICATIONS

Tokyo University of Agriculture & Technology, ATAGO.Co,Ltd, Toshitaka Wakayama, Hideki Tsujima, Yoshinori Nakashima, Yukitoshi Otani and Norihior Umeda, Lecture Collection of Japan Society of Applied Physics (JSAP); Vo. 1137 (2005), "Optical Rotation Measurement Using Liquid Crystals", 1 Page.
(Continued)

*Primary Examiner* — Abdullahi Nur
(74) *Attorney, Agent, or Firm* — Brooks Kushman P.C.

(57) ABSTRACT

A device includes a sample chamber (1) configured to receive the object, a polarization degree measuring member (2) configured to measure the polarization degree of the object received in the sample chamber (1), and a refractive index measuring member (3) configured to measure information corresponding to the refractive index of the object received in the sample chamber (1). The polarization degree measuring member (2) includes a polarization modulation member (11) configured to perform polarization modulation on a light beam (9) for analyzing the object and allow the modulated light beam to enter the sample chamber (1), an intensity detection member (12) configured to detect an
(Continued)

intensity of the light beam (5) exiting from the sample chamber, and a polarization degree calculation member (13). The refractive index measuring member (3) includes a position detection member (26) and a refractive index (concentration) calculation member (13).

3 Claims, 1 Drawing Sheet

(51) Int. Cl.
*G01N 33/02* (2006.01)
*G01N 21/21* (2006.01)
*G01J 4/04* (2006.01)
*G01N 21/17* (2006.01)

(52) U.S. Cl.
CPC ........ *G01N 2021/1734* (2013.01); *G01N 2201/068* (2013.01); *G01N 2201/0668* (2013.01)

(56) References Cited

FOREIGN PATENT DOCUMENTS

| | | |
|---|---|---|
| JP | 2005091063 A | 4/2005 |
| JP | 2005292028 A | 10/2005 |
| JP | 3814077 B2 | 8/2006 |
| JP | 2009085853 A | 4/2009 |
| WO | 2004088286 A1 | 10/2004 |
| WO | 2006052644 A2 | 5/2006 |

OTHER PUBLICATIONS

PCT Search Report & Written Opinion Dated Aug. 18, 2015, Application No. PCT/JP2015/065755, Applicant Atago Co., Ltd., 7 Pages.

Korean Office Action Dated Aug. 22, 2016, Application No. 10-2015-7024971, Applicant Atago Co., Ltd., 4 Pages.

Korean Office Action Dated Feb. 15, 2017, Application No. 10-2015-7024971, Applicant Atago Co., Ltd., 4 Pages.

\* cited by examiner

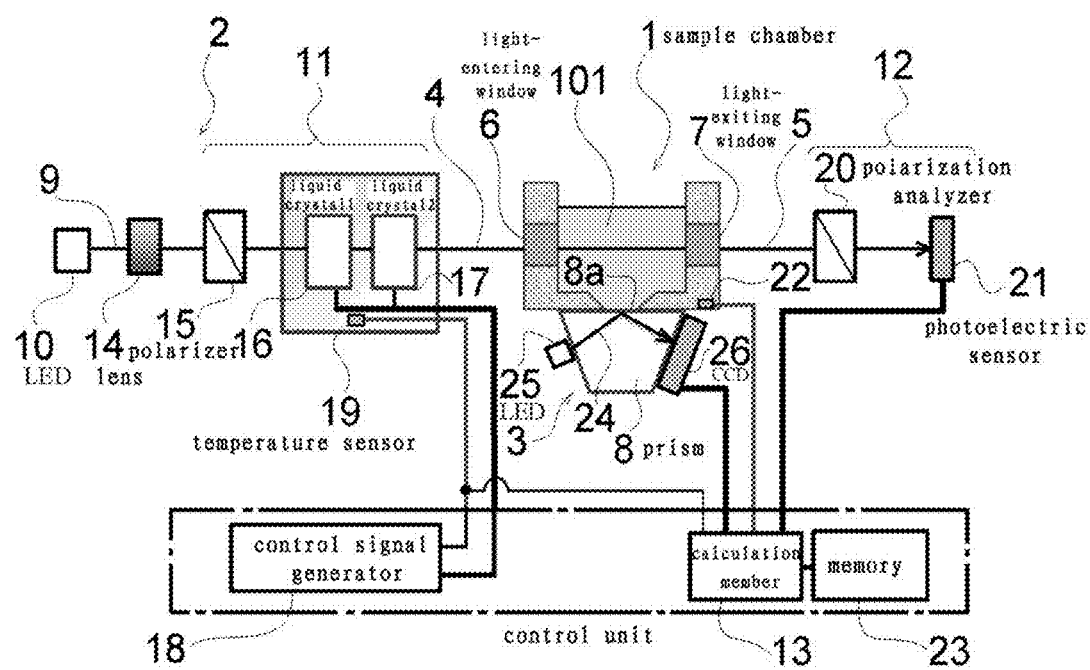

DEVICE FOR MEASURING POLARIZATION DEGREE AND REFRACTIVE INDEX

CROSS-REFERENCE TO RELATED APPLICATION

The present application is the U.S. national phase of PCT Application No. PCT/JP2015/065755 filed on Jun. 1, 2015, which claims priority to the Japanese Patent Application No. 2014-114113 filed on Jun. 2, 2014, which is incorporated herein by reference in its entirety.

TECHNICAL FIELD

The present disclosure relates to a device for measuring a polarization degree and a refractive index of a liquid or solid under an identical condition.

BACKGROUND

Such a method for measuring a refractive index of an object and converting the resultant refractive index into a concentration (a (Brix) value) is already known in the art. In addition, patent literature 1, patent literature 2 and non-patent literature 1 have each disclosed a method for measuring a polarization degree of an object by rotating a polarizer.

Moreover, for example, in order to calculate a pure sugar rate representing a sucrose content of a totally soluble solid, it is required to calculate the Brix value in accordance with the refractive index and calculate a polarization degree using a polarimeter. Then, a third parameter is calculated in accordance with the Brix value and the polarization degree.

EXISTING LITERATURES

Patent Literatures

Patent literature 1: JP2005-292028; and Patent literature 2: JP2009-085853.

Non-Patent Literature

Non-patent literature 1: Liquid Crystal Polarimeter, Toshitaka WAKAYAMA, Hideki TSUJIMA, Yoshinori NAKASHIMA, Yukitoshi OTANI and Norihiro UMEDA, Lecture Collection of Japan Society of Applied Physics (JSAP), Vol. 1137 (2005).

SUMMARY

Problem to be Solved

However, the refractive index and the polarization degree of the object need to be measured by dedicated devices, respectively. In order to calculate the third parameter in accordance with these two values, it is required to input the resultant values obtained by one device into another, and this calculation is complicated.

In addition, it is impossible to measure several values of the object simultaneously under an identical measurement condition.

Moreover, an existing polarimeter for measuring the polarization degree, as a large device, includes a driving mechanism such as an electric motor, so it is very difficult to miniaturize the polarimeter so as to measure the polarization degree conveniently.

Hence, an object of the present disclosure is to provide an easily-miniaturized, conveniently-operated device for measuring a polarization degree and a refractive index of an object simultaneously under an identical measurement condition.

Solution to the Problem

In order to solve the above-mentioned problem, the device for measuring a polarization degree and a refractive index in one embodiment of the present disclosure includes the following structures.

Structure 1

The device includes a sample chamber configured to receive an object, a polarization degree measuring member configured to measure the polarization degree of the object received in the sample chamber, and a refractive index measuring member configured to measure information corresponding to the refractive index of the object received in the sample chamber. The sample chamber is arranged in such a manner as to allow a light beam for analyzing the object to enter the sample chamber at one side, transmit through the object received in the sample chamber and then exit from the sample chamber at the other side, and a portion of a wall or bottom of a room for receiving the object is formed by one surface of a prism. The polarization degree measuring member includes a light source configured to generate the light beam for analyzing the object, a polarization modulation member configured to perform polarization modulation on the light beam for analyzing the object and allow the modulated light beam to enter the sample chamber, an intensity detection member configured to detect an intensity of the light beam exiting from the sample chamber, and a polarization degree calculation member configured to calculate polarization characteristics of the light beam for analyzing the object in accordance with the intensity detected by the intensity detection member and calculate the polarization degree of the object. The refractive index measuring member includes a light source configured to generate a light beam for analyzing the object toward the prism that forms a portion of the wall or bottom of the sample chamber, a position detection member configured to detect position information about the light beam which enters the prism and exits from the surface of the prism that forms a portion of the wall or bottom of the sample chamber, and a refractive index (concentration) calculation member configured to calculate the refractive index or concentration in accordance with the position information detected by the position detection member and corresponding to the refractive index of the object.

Structure 2

A third parameter is calculated in accordance with the polarization degree calculated by the polarization degree calculation member and the refractive index or concentration calculated by the refractive index (concentration) calculation member.

Structure 3

A Brix value is calculated by the refractive index (concentration) calculation member and the third parameter is a pure sugar rate of the object.

Technical Effect

The device for measuring the polarization degree and the refractive index in the embodiment of the present disclosure includes the sample chamber, the polarization degree measuring member and the refractive index measuring member, so as to measure the two parameters simultaneously under an identical condition, thereby to reduce the time desired for the measurement. In other words, through measuring the information corresponding to the polarization degree and the refractive index simultaneously, it is able to reduce the time desired for inputting a parameter obtained by one device into another.

Hence, the device in the embodiment of the present disclosure may be adapted to a situation where a third parameter, e.g., a pure sugar rate, is calculated in accordance with two parameters.

In addition, the device in the embodiment of the present disclosure may be miniaturized, so as to facilitate the measurement. For an existing device for measuring the polarization degree, a polarizer is rotated by an electric motor, or a large-scale, complex polarization modulator such as a Faraday cell or a Pulse Encode Modulation (PEM) is used. Hence, it is difficult to form this kind of large-scale device integrally with an existing miniature device for measuring the refractive index.

In contrast, in the device for measuring the polarization degree and the refractive index in the embodiment of the present disclosure, when a liquid crystal element is used as the polarization modulation member, it is unnecessary to provide a driving member such as an electric motor, so it is able to miniaturize the device. The liquid crystal element may be driven at a low voltage and at low power consumption. Hence, the polarization modulation member may be formed integrally with the exiting miniature device for measuring the refractive index, thereby to provide the device for measuring both the polarization degree and the refractive index.

In addition, when measuring the polarization degree of a liquid sample in the past, an observation tube with a predetermined optical path length is used. At this time, it is required to provide a mechanism including the observation tube, resulting in a constraint to the miniaturization of the device. Further, when the refractive index needs to be measured simultaneously, it is required to mount a detection member for detecting the refractive index on the observation tube, resulting in a complicated structure.

In contrast, in the device for measuring the polarization degree and the refractive index in the embodiment of the present disclosure, the sample chamber is arranged in such a manner as to allow the light beam for analyzing the object to enter the sample chamber at one side and then exit from the sample chamber at the other side, so it is unnecessary to provide the observation tube, thereby it is able to simplify and miniaturize the device.

In a word, the present disclosure provides in the embodiment the easily-miniaturized, conveniently-operated device for measuring the polarization degree and the refractive index of the object simultaneously under an identical measurement condition.

BRIEF DESCRIPTION OF THE DRAWINGS

FIG. 1 is a block diagram of a device for measuring a polarization degree and a refractive index according to one embodiment of the present disclosure.

DETAILED DESCRIPTION

Brief Description about a Device for Measuring a Polarization Degree and a Refractive Index in One Embodiment of the Present Disclosure As shown in FIG. 1, the device for measuring the polarization degree and the refractive index according to one embodiment of the present disclosure includes a sample chamber 1 configured to receive an object 101, a polarization degree measuring member 2 configured to measure the polarization degree of the object 101 received in the sample chamber 1, and a refractive index measuring member 3 configured to measure the refractive index of the object 101 received in the sample chamber 1.

The object 101 may be directly injected into the sample chamber 1, and the sample chamber 1 is arranged in such a manner as to allow a light beam 4 entering the sample chamber 1 at one side for analyzing the object to be transmitted through the object 101 received in the sample chamber 1 and then exit from the sample chamber 1 at the other side. To be specific, an opening at one side of the sample chamber 1 is closed with the transparent material so as to form a light-entering window 6, and an opening at the other side of the sample chamber 1 is closed with the transparent material so as to form a light-exiting window 7. The transparent material may be a material through which a polarization state of the light beam is not changed, or a material through which a change in the polarization state of the light beam is already known.

In addition, in the sample chamber 1, a portion of a wall or bottom of a room for receiving the object 101 is formed by a surface 8a of a prism 8 of the refractive index measuring member 3. In the embodiment of the present disclosure, the surface 8a of the prism 8 forms a portion of the bottom of the room for receiving the object 101.

The polarization degree measuring member 2 includes a light source 10 configured to generate a light beam 9 for analyzing the object 101, and a polarization modulation member 11 configured to perform polarization modulation on the light beam 9 for analyzing the object 101 and then allow the light beam 9 to enter the sample chamber 1 through the light-entering window 6. The light source 10 may be, e.g., a monochromatic light emitting diode (LED). The light beams 9 from the light source 10 are transmitted through a condenser lens 14 and then converted into parallel light beams.

The polarization modulation member 11 includes a polarizer 15 configured to merely allow a predetermined polarized light component to be transmitted therethrough, a first liquid crystal element 16 and a second liquid crystal element 17. Voltages are applied onto the liquid crystal elements 16, 17 under the control of a control signal generator 18. In addition, temperatures of the liquid crystal elements 16, 17 are detected by a temperature sensor 19, and temperature information is then sent to the control signal generator 18. The liquid crystal elements 16, 17 are controlled by the control signal generator 18 to be each in a predetermined polarization state in accordance with the temperature information from the temperature sensor 19. Alternatively, the voltages applied onto the liquid crystal elements 16, 17 are not controlled, and instead, the polarization degree may be calculated and modified in accordance with the temperature information about the liquid crystal elements 16, 17 from the temperature sensor 19.

The polarization degree measuring member 2 includes an intensity detection member 12 configured to detect an intensity of the light beam 5 exiting from the light-exiting window 7 of the sample chamber 1. In the device for measuring the polarization degree and the refractive index, the intensity of the light beam 5 exiting from the light-exiting window 7 varies along with the polarization degree of the object 101 within the sample chamber 1.

The intensity detection member 12 includes a polarization analyzer 20 and a photoreceptive sensor (photoelectric sensor) 21. The light beam 5 exiting from the light-exiting window 7 is transmitted through the polarization analyzer 20 and then received by the photoreceptive sensor 21, and the intensity information detected by the intensity detection member 12 is sent to the polarization degree calculation member 13. In addition, a temperature of the sample chamber 1 is detected by a temperature sensor 22, and the resultant temperature information is then sent to the polarization degree calculation member 13 too.

The polarization degree calculation member 13 calculates the polarization characteristics of the light beam 5 for analyzing the object in accordance with the intensity information detected by the intensity detection member 12 and the temperature information detected by the temperature sensor 22, and then calculates the polarization degree of the object 101. A calculation result obtained by the polarization degree calculation member 13 is stored in a memory 23.

In addition, the polarization degree calculation member 13, together with the under-mentioned refractive index (concentration) calculation member, forms a calculation member 13.

The refractive index measuring member 3 includes a light source 25 configured to generate a light beam 24 (a diffused light beam) for analyzing the object and the light beam enters the prism 8. The light source 25, as a point light source, may be, e.g., a monochromatic LED.

The light beam 24 entering the prism 8 is entered onto a surface 8a of the prism 8 that forms a portion of the bottom of the sample chamber 1 and internally reflected by the surface 8a of the prism 8, and then exits from another surface of the prism 8 toward the position detection member 26, e.g., a charge coupled device (CCD), so that the position detection member 26 may detect a position of the light beam 24 exiting from the other surface of the prism 8 after being internally reflected by the surface 8a.

In the device for measuring the polarization degree and the refractive index, the position of the light beam 24 exiting from the other surface of the prism 8 after being internally reflected by the surface 8a varies along with the refractive index of the object 101 within the sample chamber 1. The surface 8a of the prism 8 is an interface between the prism 8 and the object 101, and a critical angle of the surface 8a is determined in accordance with the refractive index of the object 101. The position information about the light beam 24 corresponds to the refractive index of the object 101.

In addition, the light beam for the refractive index measuring member 3 may also be a parallel light beam. In this case, the position information about the light beam that passes through the object 101 and the surface 81 of the prism 8 (the interface between the prism 8 and the object 101) and then exits from the other surface of the prism 8 may be detected. This position information also corresponds to the refractive index of the object 101.

The position information detected by the position detection member 26 is sent to the refractive index (concentration) calculation member 13. In the embodiment of the present disclosure, the refractive index (concentration) calculation member 13 calculates a Brix value of the object 101 in accordance with the received position information about the light beam 24. The Brix value may be directly calculated in accordance with the position information about the light beam 24, or the refractive index of the object 101 may be calculated in accordance with the position information and then converted into the Brix value. Regardless of the calculation methods, the Brix value is calculated in accordance with the position information corresponding to the refractive index of the object 101.

In addition, during the calculation, the Brix value may be modified in accordance with the temperature information (the temperature of the object 101) from the temperature sensor 22 in the sample chamber 1.

In addition, in the device for measuring the polarization degree and the refractive index, a third parameter, e.g., a pure sugar rate of the object 101, may be calculated in accordance with the polarization degree calculated by the polarization degree calculation member 13 and the Brix value calculated by the refractive index (concentration) calculation member 13.

[Example about the Structure of the Device for Measuring the Polarization Degree and the Refractive Index]

A monochromatic LED with a light-emitting wavelength of about 590 nm is used as the light source 10 of the polarization degree measuring member 2. The light beam 9 for analyzing the object passes through a pinhole of $\phi 0.4$ mm, converted by a biconvex lens 14 with a focal length of 9 mm into a parallel light beam, and then modulated by the polarization modulation member 11 including the polarizer 15 and the liquid crystal elements 16, 17. Directions of the polarizer 15 and the liquid crystal elements 16, 17 are set as 0°, 45° and 0°, respectively, and the liquid crystal elements 16,17 are driven by an alternating voltage from the control signal generator 18. The liquid crystal elements 16, 17 each include nematic liquid crystals with $\Delta n 0.2$ and a cell gap of 5.5 μm.

The light beam 4 for analyzing the object obtained after the polarization modulation by the polarization modulation member 11 is transmitted through the object 101 within the sample chamber 1, so as to rotate the light beam. The light beam 4 enters the sample chamber 1 through the light-entering window 6 at a left side of the sample chamber 1, passes through the object 101, and then exits from the light-exiting window 7 at a right side of the sample chamber 1. The light-entering window 6 and the light-exiting window 7 may each be made of a transparent material, e.g., BK-7. In addition, a distance between the light-entering window 6 and the light-exiting window 7 is set as 20 mm. The light beam 5 passing through the object 101 is transmitted through the polarization analyzer 20 with the direction of 90°, and then detected by the photoreceptive sensor 21. The method for measuring the polarization degree by the polarization degree measuring member 2 is known in the art, and thus will not be particularly defined herein.

A monochromatic LED having a light-emitting wavelength of about 590 nm is also used as the light source 25 of the refractive index measuring member 3. The light beam 24 for analyzing the object from the point light source is diffused within the prism 8, and then reflected by, or transmitted through, the surface 8a of the prism 8 that forms a portion of the bottom of the room for receiving the object 101. The reflected light beam 24 exits from the other surface of the prism 8, and the position information about the light beam 24 is then detected by the position detection member 26. This position information detected by the position detection member 26 is information about bright and dark states generated at a reflection-transmission boundary, i.e., a critical angle, of the surface 8a of the prism 8, and it corresponds to the refractive index of the object 101. A CCD linear sensor is used as the position detection member 26. In addition, the prism 8 is made of SF-2.

[Example for Testing the Pure Sugar Rate Using the Device for Measuring the Polarization Degree and the Refractive Index]

The pure sugar rate may be calculated by the following equation: the pure sugar rate [%]=(a sucrose content/a totally soluble solid)×100. The totally soluble solid is represented by a Brix value [%]. The sucrose content may be calculated by the following equation: the sucrose content= (26.016/a mass (density) of a 100 ml liquid)×an international sugar scale.

In addition, the mass of the 100 ml liquid is calculated using an equation (2) as defined in Item 4 of International Commission for Uniform Methods of Sugar Analysis (ICUMSA) Specification and Standard (SPS)-4. Furthermore, for the international sugar scale, the polarization degree of a sucrose solution with a concentration of 26.000 g/100 ml tested by the 200 mm observation tube is set as 100° Z and defined in Item 3.2 of ICUMSA SPS-1 (see Conferences of ICUMSA (Japan): ICUMSA Methods Book, SPS-1(2005) pp. 1-7; and ICUMSA Methods Book, SPS-4 (1994) pp. 〔71〕1-〔71〕11).

Depending on the above, the pure sugar rate may be calculated in accordance with the measured polarization degree and Brix value. The following Table 1 shows the measurement results for three samples with sucrose contents of 10% (w/w), 20% (w/w) and 30% (w/w), respectively.

TABLE 1

|  | Polarization degree (°) | Brix value (%) | Pure sugar rate (%) |
|---|---|---|---|
| Sucrose content 10% | 1.38 | 10.0 | 99 |
| Sucrose content 20% | 2.88 | 20.0 | 100 |
| Sucrose content 30% | 4.51 | 30.0 | 100 |

Due to the absence of impurities, the pure sugar rate of each of the three samples is approximately 100%.

INDUSTRIAL APPLICABILITY

The device in the embodiment of the present disclosure may be used to measure a polarization degree and a refractive index of a liquid or solid under an identical condition.

REFERENCE NUMERALS 1 sample chamber
2 polarization degree measuring member
3 refractive index measuring member
4, 5, 9, 24 light beams for analyzing object
8 prism
8a surface
10, 25 light sources
11 polarization modulation member
12 intensity detection member
13 polarization degree calculation member and refractive index (concentration) calculation member
26 position detection member
101 object

What is claimed is:

1. A device for measuring a polarization degree and a refractive index, comprising:
 a sample chamber configured to receive an object;
 a polarization degree measuring member configured to measure the polarization degree of the object received in the sample chamber; and
 a refractive index measuring member configured to measure information corresponding to the refractive index of the object received in the sample chamber, wherein
 the sample chamber is arranged in such a manner as to allow a light beam for analyzing the object to enter the sample chamber at one side, transmit through the object received in the sample chamber and then exit from the sample chamber at the other side, and a portion of a wall or bottom of a room for receiving the object is formed by one surface of a prism;
 the polarization degree measuring member comprises a light source configured to generate the light beam for analyzing the object, a polarization modulation member configured to perform polarization modulation on the light beam for analyzing the object and allow the modulated light beam to enter the sample chamber, an intensity detection member configured to detect an intensity of the light beam exiting from the sample chamber, and a polarization degree calculation member configured to calculate polarization characteristics of the light beam for analyzing the object in accordance with the intensity detected by the intensity detection member and calculate the polarization degree of the object; and
 the refractive index measuring member comprises a light source configured to generate a light beam for analyzing the object toward the prism that forms a portion of the wall or bottom of the sample chamber, a position detection member configured to detect position information about the light beam which enters the prism and exits from the surface of the prism that forms a portion of the wall or bottom of the sample chamber, and a refractive index (concentration) calculation member configured to calculate the refractive index or concentration in accordance with the position information detected by the position detection member and corresponding to the refractive index of the object.

2. The device according to claim 1, wherein a third parameter is calculated in accordance with the polarization degree calculated by the polarization degree calculation member and the refractive index or concentration calculated by the refractive index (concentration) calculation member.

3. The device according to claim 2, wherein a Brix value is calculated by the refractive index (concentration) calculation member and the third parameter is a pure sugar rate of the object.

* * * * *